(12) United States Patent
Lau et al.

(10) Patent No.: US 6,303,792 B1
(45) Date of Patent: Oct. 16, 2001

(54) PROCESS FOR CRYSTALLIZING N-(4-TRIFLUOROMETHYLPHENYL)-5-METHYLISOXAZOLE-4-CARBOXAMIDE

(75) Inventors: Hans-Hermann Lau, Bad Soden; Udo Hedtmann, Frankfurt; Holger Faasch, Alzey; Andreas Gappisch, Gross-Gerau, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/510,157

(22) Filed: Feb. 22, 2000

(30) Foreign Application Priority Data

Feb. 26, 1999 (DE) .............................................. 199 08 527

(51) Int. Cl.$^7$ ................................................. C07D 261/14
(52) U.S. Cl. .............................................................. 548/248
(58) Field of Search ............................................... 548/248

(56) References Cited

U.S. PATENT DOCUMENTS

| 4,284,786 | 8/1981 | Kämmerer et al. | 548/248 |
| 4,351,841 | 9/1982 | Kammerer et al. | 424/272 |
| 4,965,276 | 10/1990 | Bartlett et al. | 514/378 |
| 5,494,911 * | 2/1996 | Bartlett et al. | 514/256 |
| 5,519,042 * | 5/1996 | Morris et al. | 514/378 |
| 6,060,494 | 5/2000 | Faasch et al. | 514/378 |

* cited by examiner

*Primary Examiner*—Deborah C. Lambkin
*Assistant Examiner*—Ebenezer Sackey
(74) *Attorney, Agent, or Firm*—Finnegan, Henderson, Farabow, Garrett, & Dunner, L.L.P.

(57) ABSTRACT

The invention relates to a process for obtaining N-(4-trifluoromethylphenyl)-5-methyl-isoxazole-4-carboxamide in crystalline form, which is essentially free of byproducts. For this purpose, N-(4-trifluoromethylphenyl)-5-methylisoxazole-4-carboxamide is transferred into an organic solvent or into mixtures of organic solvents and water, the amount of byproduct in the solution is determined by quantitative analysis and an equimolar amount of a base is added. N-(4-Trifluoromethylphenyl)-5-methyl-isoxazole-4-carboxamide is isolated from the resulting solution by crystallization.

33 Claims, No Drawings

PROCESS FOR CRYSTALLIZING N-(4-TRIFLUOROMETHYLPHENYL)-5-METHYLISOXAZOLE-4-CARBOXAMIDE

The invention relates to a process for obtaining N-(4-trifluoromethylphenyl)-5-methyl-isoxazole-4-carboxamide in crystalline form, which is essentially free of byproducts. The compound of the formula I

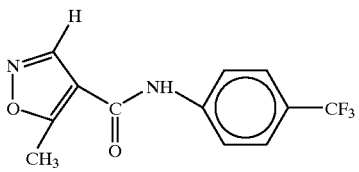

is known per se and is also referred to as N-(4-trifluoromethylphenyl)-5-methyl-isoxazole4-carboxamide or leflunomide (HWA 486). The compound of the formula I can be obtained by the method described in U.S. Pat. No. 4,284,786. In said patents, processes for crystallization from toluene are also described.

The disadvantage of the known processes for obtaining compounds of the formula I is that byproducts such as N-(4-trifluoromethylphenyl)-2-cyano-3-hydroxy-crotonamide (compound 2 below) essentially cannot be separated by crystallization from solutions containing the compound of the formula I and the compound 2. The compound 2 is described, for example, in U.S. Pat. No. 4,965,276.

The object of the invention is to provide, by modifying the process conditions, a compound of the formula I in high yields which is essentially free of N-(4-trifluoromethylphenyl)-2-cyano-3-hydroxycrotonamide.

The object is achieved by transferring the compound of the formula 1, containing compound 2 as byproduct, into an organic solvent or into mixtures of organic solvent and water, determining the amount of compound 2 in the solution by an appropriate method of analysis and adding an approximately equimolar amount of a base, for example $NaHCO_3$ or $KHCO_3$, and separating the compound of the formula I by crystallization from the solution obtained.

The invention therefore relates to a process for obtaining the compound of the formula I

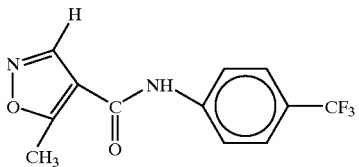

from a solution containing water, at least one organic solvent, the compound of the formula I and N-(4-trifluoromethylphenyl)-2-cyano-3-hydroxycrotonamide, which comprises a) quantitatively determining the amount of N-(4-trifluoromethylphenyl)-2-cyano-3-hydroxycrotonamide in the solution, b) adding the amount of a base which corresponds to from 50 mol % to 150 mol % of the amount determined in a), c) crystallizing the compound of the formula I and d) separating the resulting crystals of the compound of the formula I from the solution.

As a result of adding the base, N-(4-trifluoromethylphenyl)-2-cyano-3-hydroxycrotonamide remains in the solution and is not separated off together with the compound of the formula I during the crystallization. Smaller or larger amounts than the amount of added base defined under b) lead to increased byproduct formation and reduce the yield of the compound of the formula I.

For obtaining the compound of formula I, for example, the compound of formula I is dissolved in a solvent. Suitable solvents are, for example, water-miscible solvents, such as $(C_1-C_4)$-alcohols, e.g. methanol, ethanol, propanol, isopropanol, butanol or isobutanol, but also ketones, such as acetone or methyl ethyl ketone. Water is then added. Mixtures of organic solvents with water, for example of about 40% to 90% of isopropanol, have also proven useful. The dissolution process is preferably carried out at elevated temperature up to the boiling point of the respective solvent.

In the solution obtained, the amount of N-(4-trifluoromethylphenyl)-2-cyano-3-hydroxycrotonamide is determined. Suitable methods of determination are customary quantitative methods of measurement, such as high pressure liquid chromatography (HPLC) or alkalimetric titration. A sample is taken from the solution, and the amount of compound 2 is determined in a standard apparatus. The base is then added to the solution. With the addition of 70 mol % to 130 mol %, based on the determined amount of N-(4-trifluoromethylphenyl)-2-cyano-3-hydroxycrotonamide (compound 2), good results are obtained by HPLC. If the amount of compound 2 is determined by alkalimetric titration, amounts of 95 mol % to 105 mol % are advantageous. The quantitatively determined amount of the compound 2 is taken in each case as 100%, and the corresponding molar amount of the base added in each case is determined. It is preferable to add 85 mol % to 120 mol %, particularly preferably 100 mol % to 115 mol %, very particularly preferably 108 mol % to 112 mol %. The base may be added in dissolved or in solid form; the addition in dissolved form is preferred.

The order in which the components water, solvent, compound of the formula I and base are dissolved may also differ from the abovementioned order. For example, the base may be added before the addition of the solvent, water may be added before the addition of the solvent, or the base is not added until the solution has been heated up.

Suitable bases are, for example, organic bases, such as mono-, di- or trialkylamine, e.g. trimethylamine, triethylamine, tripropylamine, tributylamine, triisobutylamine, tripentylamine, trihexylamine, dibutylmethylamine, dimethylamine or diethylamine, the alkylamines being unsubstituted or monosubstituted to trisubstituted by phenyl or benzyl, aromatic amines, such as aniline and substituted anilines, unsubstituted and substituted heterocyclic amines, such as pyridine, piperidine, pyrrole, indole, pyrazine, pyrimidine, morpholine, pyrazole or imidazole, e.g. $(C_1-C_4)$-alkylpyridine. Further suitable bases are inorganic bases, such as sodium bicarbonate ($NaHCO_3$), sodium carbonate ($Na_2CO_3$), potassium bicarbonate ($KHCO_3$), potassium carbonate ($K_2CO_3$), sodium hydrogen phosphate ($Na_2HPO_4$), sodium dihydrogen phosphate ($NaH_2PO_4$), trisodium phosphate ($Na_3PO_4$), potassium hydrogen phosphate ($K_2HPO_4$), potassium dihydrogenphosphate ($KH_2PO_4$) or tripotassium phosphate ($K_3PO_4$), preferably $NaHCO_3$.

The solution or suspension obtained is heated and is kept at the boiling point for some time in order to ensure complete solution of the compound of the formula I.

Thereafter, the optionally filtered solution is cooled so slowly that crystals of the compound of the formula I form. Cooling preferably takes place to the final temperatures of 20° C. to −10° C., in particular to temperatures of 10° C. to −5° C., very particularly preferably to temperatures of 1° C. to 5° C. The crystals are isolated and optionally washed with isopropanol and then with water. The substance is dried at elevated temperature, preferably at 60° C, under reduced pressure or at atmospheric pressure. Other crystallization methods, such as evaporative crystallization or displacement crystallization, are also possible.

A preferred process comprises dissolving the compound of the formula I in 80% strength isopropanol at the boiling point of isopropanol under atmospheric pressure or reduced pressure, carrying out the determination of the amount of N-(4-trifluoromethylphenyl)-2-cyano-3-hydroxycrotonamide by HPLC, adding the equimolar amount of base and then cooling the hot solution slowly so that the crystallization takes place at temperatures of more than 40° C., preferably from 40° C. to 85° C., particularly preferably from 45° C. to 80° C., in particular from 50° C. to 70° C. The crystals which have separated out are then washed several times with isopropanol and dried under reduced pressure. The crystallization can be effected without seeding with crystals of the compound of the formula I or preferably in the presence of crystals of the compound of the formula I, which are introduced into the solution by seeding. Seeding can also be effected several times at various temperatures. The amount of the seed material depends on the amount of the solution and can readily be determined by a person skilled in the art.

A particularly preferred process for obtaining the compound of the formula I from a solution containing water, at least one organic solvent, the compound of the formula I and N-(4-trifluoromethylphenyl)-2-cyano-3-hydroxycrotonamide comprises a) determining the amount of N-(4-trifluoromethylphenyl)-2-cyano-3-hydroxy-crotonamide in the solution by alkalimetric titration, b) adding the approximately equimolar amount of a base, c) heating the solution obtained to a temperature from 41° C. up to the boiling point of the organic solvent, d) diluting the resulting solution with water or distilling off the organic solvent so that the organic solvent and the water are preferably present in a ratio of from 4:1 to 0.3:1 and d) carrying out the crystallization at temperatures above 40° C.

Preferably, the solution obtained is filtered after process step b).

The abovementioned bases are suitable; sodium bicarbonate, sodium carbonate and potassium bicarbonate are particularly preferred. Good results are obtained with the addition of 90 mol % to 110 mol % of the base, based on the determined amount of compound 2, determined by alkalimetric titration. The quantitatively determined amount of the compound 2 is taken in each case as 100%, and the corresponding molar amount of the base added in each case is then determined. It is preferable to add from 95 mol % to 105 mol %, particularly preferably from 98 mol % to 102 mol %.

Advantageous mixtures contain organic solvent and water in the ratio of 1:1 to 8:1, preferably of 2:1 to 6:1, in particular of 3:1 to 5:1.

The preparation of the solution is preferably carried out at elevated temperature, in particular at temperatures of 41° C. up to the boiling point of the respective solvent. The heated solution is, for example, kept at the boiling point for some time in order to ensure complete dissolution of the compound of the formula I. The dissolution process can also be carried out at superatmospheric pressure. The solution is then filtered. The filter used has a pore diameter of about 0.1 μm to 200 μm. Water, which advantageously has the same temperature as the filtered solution, is then added to the filtered solution, or the organic solvent is distilled off. The solutions obtained advantageously contain the organic solvent and water in the ratio of 4:1 to 0.3:1, preferably of 2:1 to 0.6:1, particularly preferably of 1.6:1 to 0.8:1. Cooling is then carried out slowly to a minimum temperature of 40° C. The crystals are isolated and washed with isopropanol and then with water. Drying of the substance is advantageously effected at elevated temperature, preferably at 60° C., under reduced pressure or atmospheric pressure.

A particularly preferred rocess comprises dissolving the compound of the formula I in a mixture of isopropanol and water in the ratio of 4:1 to 5:1 and at the boiling point of isopropanol under atmospheric pressure or reduced pressure and filtering the solution. Water at the same temperature as the hot solution is then added to said solution in an amount such that a ratio of isopropanol to water of 2:1 to 0.8:1 is present. The crystallization is then carried out at temperatures of more than 40° C., preferably of 40° C. to 85° C., particularly preferably of 45° C. to 80° C., in particular of 50° C. to 70° C. The crystals which have separated out are then washed several times with isopropanol and dried under reduced pressure. Purity of better than 99.9% and residual content of N-(4-trifluoromethylphenyl)-2-cyano-3-hydroxy-crotonamide of less than 0.05%, determined by high pressure liquid chromatography (HPLC), are advantageous in the recovery, according to the invention, of the compound of the formula I.

EXAMPLE 1

Stability of Leflunomide to Sodium Bicarbonate

In experiment a), 40 g of the compound of formula I were dissolved in 80 ml of isopropanol and 63 ml of water (ratio isopropanol to water 1.27:1) and stirred for 1 hour (h) at 84° C. Thereafter, a sample was taken and was quantitatively analyzed by HPLC. 0.62 g of $NaHCO_3$,5 mol % based on the compound of the formula I, was then added and stirring was continued for 5 h at 84° C.

In experiment b), a ratio of isopropanol to water of 4:1 was used and the experiment was carried out analogously to a), except that the temperature was 80° C. The formation of N-(4-trifluoromethylphenyl)-2-cyano-3-hydroxycrotonamide (compound 2) was monitored by HPLC measurement as a function of time.

The results of the HPLC measurement and pH of the individual measurements are summarized in Tables 1 and 2. Table 1 shows the formation of the compound 2 in the absence of sodium bicarbonate, while Table 2 shows the formation of the compound 2 in the presence of sodium bicarbonate.

TABLE 1

| | Isopropanol to water 1.27:1 | | | |
|---|---|---|---|---|
| Time (min) | Compound 2 (% by area) | Compound of the formula I (% by area) | pH | Remark |
| 0 | 0.026 | 99.88 | 4.0 | without NaHCO$_3$ |
| 60 | 0.082 | 99.82 | 4.0 | without NaHCO$_3$ |

In experiment a) (Table 1), a pH of 4.0 was measured in the starting solution, and the value was unchanged even after 1 h. The amount of compound 2 increased in this time from 0.026 percent by area (% by area) to 0.082% by area. In experiment b) (as Table 1), no determination of the pH or of the amount of compound 2 was carried out.

TABLE 2

| | Isopropanol to water 1.27:1 (Experiment a)) | | | Isopropanol to water 4:1 (Experiment b)) | |
|---|---|---|---|---|---|
| Time (min), | Compound 2 (% by area) | Compound of the formula I (% by area) | pH | Compound 2 (% by area) | PH |
| 0 | 3.4 | 96.56 | 8.5 | n.d. | n.d. |
| 30 | 6.63 | 93.36 | 4.9 | 4.30 | n.d. |
| 60 | 6.80 | 93.17 | 4.5 | 4.51 | n.d. |
| 120 | 6.93 | 93.02 | 4.4 | 4.68 | n.d. |
| 180 | 7.10 | 92.78 | 4.3 | 5.02 | 5.7 |
| 300 | 7.22 | 92.59 | 4.3 | 5.56 | 5.7 | n.d. means not determined

In experiment a) (Table 2), a pH of 8.5 was measured in the solution directly after the addition of sodium bicarbonate, and the pH decreased to 4.3 in the course of 5 hours. The formation of the compound 2 after the addition of sodium bicarbonate took place very rapidly. Immediately after the addition of sodium bicarbonate, 3.4% by area of the compound 2 were detectable, and as much as 6.6% by area after 30 minutes (min). After 5 h, an amount of 7.2% by area was reached. In experiment b), the formation of the compound was comparably rapid. An amount of 5.6% by area of the compound 2 was reached after 5 h.

The results clearly show that an excess of sodium bicarbonate essentially leads to the formation of the compound 2. Because, depending on the batch for the preparation of the compound I, the content of the compound 2 may vary, it is important to determine the required amount of sodium bicarbonate beforehand by quantitative analysis of the amount of compound 2. This is carried out, for example, by HPLC or alkalimetric titration.

Quantitative HPLC determination

| | |
|---|---|
| Apparatus: | Liquid chromatograph (Waters 2690 with PDA detector 996) |
| Column: | Material: stainless steel |
| | Length: 125 mm |
| | Internal diameter: 4 mm |
| Stationary phase: | Lichrospher ® 100 RP 18 endcapped, particle size 5 μm |
| Mobile phase: | acetonitrile 350 parts by volume |
| | water 650 parts by volume |
| | triethylamine 5 parts by volume |
| | pH was adjusted to 4.0 with 85% phosphoric acid. |
| Injected volume: | 10 μl |
| Flow rate: | 1.0 ml/min |
| Detection: | UV/Vis, 210 nm |
| Run time: | 40 min |
| Test solution: | About 20.0 mg of the substance to be investigated were dissolved in 4 ml of acetonitrile and made up to 20.0 ml with mobile phase. |
| Calculation: | The content of compound 2 was calculated by calculating the arithmetic mean of all injections. |

$$\frac{A \cdot 100}{B} = \text{content of compound 2 in \%}$$

A = peak area of compound 2 in the chromatogram of the test solution.
B = sum of the peak areas in the chromatogram of the test solution.

System test:

System test solution: 20 mg of 4-trifluoromethylaniline (4-TFMA) are diluted to 10.0 ml with mobile phase (SS1).
30 mg of compound 2 and 10 mg of 3-TFMP-isomer were weighed in. 1.0 ml of the solution SS1 and 5 ml of acetonitrile were added. The mixture obtained was made

| | -continued |
|---|---|
| | up to 100.0 ml with mobile phase (SS2) and shaken until the solution was clear.
100 mg of the compound of the formula I (leflunomide reference standard) were dissolved in 2 ml of acetonitrile, 1.0 ml of SS2 was added and the solution was made up to 100.0 ml with mobile phase (SS3).
SS3 had the following concentration: 1 mg/ml of leflunomide; 0.003 mg/ml of compound 2; 0.0001 mg/ml of 3-TFMP-isomer; 0.0002 mg/ml of 4-TFMA. |
| Selectivity: | The chromatogram of the standard solution SS3 had to meet the following requirements:
Compound 2 Relative retention time: about 0.13 to 0.23
4-TFMA Relative retention time: about 0.36 to 0.44
Leflunomide Absolute retention time: about 22 to 35 |
| Abbreviations: | 4-TFMA: 4-Trifluoromethylaniline
3-TFMP: N-(3'-Trifluoromethylphenyl)-5-methylisoxazole-4-carboxamide |
| Alkalimetric titration | |
| Apparatus: | Titrator with automatic end point detection (e.g. Metrohm Titroprocessor 716) |
| Electrode: | combined glass electrode (e.g. Mettler Toledo DG 112-SC) |
| Factor of the standard solution: | 0.05 g of succinic acid was dissolved in 50 ml of water and titrated with 0.1 N sodium hydroxide solution. |
| Procedure: | 1.0 g of the substance to be tested was dissolved in 50 ml of methanol and immediately titrated with 0.1 N sodium hydroxide solution. |
| Calculation (factor of 0.1 N sodium hydroxide solution): | $\frac{W \cdot 1000}{C \cdot 59.05}$ = factor of the 0.1 N sodium hydroxide solution |

C = Consumption of 0.1 N sodium hydroxide solution
  (1 ml of 0.1 N sodium hydroxide solution is equivalent to 59.05 mg succinic acid)
W = Weight of succinic acid taken, in g Calculation: $\frac{C \cdot F \cdot 27.02}{W}$ = Compound 2 (in %)

C = Consumption of 0.1 N sodium hydroxide solution, in ml
F = Factor of 1 N hydrochloric acid
W = Weight of the substance to be tested in g

EXAMPLE 2

Crystallization in the Presence of NaHCO₃

16 kg of the compound of the formula I (leflunomide) were dissolved in 28 liters (l) of isopropanol and water so that the total amount of water was 9 l. The amount of the compound 2 in the solution obtained was then determined by alkalimetric titration. The equimolar amount of sodium bicarbonate was calculated and was added in solid form to the solution (cf. Table 3). Thereafter, heating to 78° C. to 82° C. was carried out, stirring was effected for 25 min at this temperature and filtration was then effected through a suction filter into a vessel likewise already heated to the same temperature. The suction filter was then rinsed with the amount of isopropanol which, together with isopropanol used, gave an isopropanol/water ratio of 4:1 (in this case about 4 l). 32 l of water, likewise preheated to from 78° C. to 82° C., was then added (gave an isopropanol/water ratio of 0.8:1). The solution became turbid and was then cooled to about 65° C. in 20 min, kept at this temperature for about 40 min, then cooled to about 40° C in 70 min and stirred for a further 20 min. The crystalline compound of the formula I was isolated by centrifugation.

Table 3 summarizes the results of three different crystallizations.

TABLE 3

| Leflunomide before crystallization [kg] | Compound 2 before crystallization [%] | NaHCO₃ [kg] | Yield of leflunomide after crystallization [kg] | Yield of leflunomide after crystallization [%] | Compound 2 after crystallization (HPLC) [% by area] | Purity of leflunomide after crystallization (HPLC) [% by area] |
|---|---|---|---|---|---|---|
| 17.19 | 2.44 | 0.13 | 12.7 | 79.3 | 0.03 | 99.9 |
| 17.15 | 2.20 | 0.12 | 12.8 | 80.0 | 0.02 | 99.7 |
| 16.97 | 3.22 | 0.17 | 12.6 | 78.8 | 0.02 | 99.9 |

An average yield of 79.4% of theory with only very small deviations within the individual batches was achieved (±0.6%), a purity of on average 99.93% (HPLC, % by area)

was obtained. The amount of the compound 2 in the individual batches according to HPLC determination was from 0.02% by area to 0.04% by area.

EXAMPLE 3

Crystallization in the Presence of $NaHCO_3$ 50 g of the compound of the formula I, containing 0.46% of the compound 2 —the determination of the amount of the compound 2 was carried out by HPLC measurement —were added to 25 ml of isopropanol and 25 ml of water; 28.65 mg of $NaHCO_3$ were then added and the suspension obtained was stirred at room temperature of about 21° C. for 15 to 30 minutes. Thereafter, 76. ml of isopropanol and 1 g of active carbon were added, heating was carried out to 80° C. and filtration was effected through a suction filter. The filtrate obtained was cooled to 60° C., seeded with a few crystals of the compound of the formula I and then cooled to 0° C. to 5° C. The crystals obtained were filtered off with suction and washed with 37.5 ml of isopropanol and 3 times with 125 ml of water. The yield was 77% of the compound of the formula I and the purity was more than 99.9% according to HPLC measurement. The content of the compound 2 according to HPLC measurement was less than 0.01 %, based on the compound of the formula I as 100%.

EXAMPLE 4

Comparative Example for Crystallization without Sodium Bicarbonate 50 g of the compound of the formula I, containing 1.7% of the compound 2 —the determination of the amount of the compound 2 was carried out by HPLC measurement —were suspended in 93.75 ml of isopropanol and 25 ml of water. After the addition of 1 g of active carbon, the suspension obtained was heated to 84° C. and filtered through a suction filter. The filtered solution was washed with 6.25 ml of isopropanol. The solution was cooled to room temperature of about 21 ° C. in the course of 2 hours. Thereafter, the solution was cooled to 0° C in the course of 30 minutes and this temperature was maintained for 2 hours until the solution was filtered through a suction filter. The filter cake obtained was washed with two 6.25 ml portions of water. The crystals of the compound of the formula I were dried at 50° C. under reduced pressure. Yield: 41.8 g of the compound of the formula I, purity 99.1% according to HPLC measurement. The content of the compound 2 was determined by HPLC measurement as 0.86%, based on the compound of the formula I as 100%.

We claim:

1. A process for separating a compound of formula I

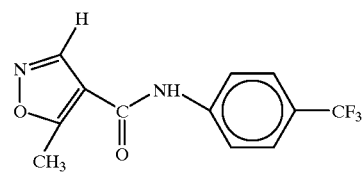

(I)

from a solution comprising water, at least one organic solvent, a compound of formula I, and n-(4-trifluoromethylphenyl)-2-cyano-3-hydroxycrotonamide, comprising
   a) quantitatively determining the amount of N-(4-trifluoromethylphenyl)-2-cyano-3-hydroxycrotonamide in the solution,
   b) adding base corresponding to from about 50 mol % to about 150 mol % of the amount of the quantitatively determined N-(4-trifluoromethylphenyl)-2-cyano-3-hydroxycrotonamide,
   c) crystallizing the compound of formula I, and
   d) separating the resulting crystals of the compound of formula I from the solution.

2. The process according to claim 1, wherein the base is an organic base.

3. The process according to claim 1, wherein the base is selected from the group consisting of an unsubstituted, monosubstituted, disubstituted, or trisubstituted alkyl amine wherein the substituents are selected from benzyl and phenyl; an unsubstituted or substituted heterocycloalkyl amine; and an inorganic base.

4. The process according to claim 3, wherein the base is selected from the group consisting of trialkylamines, aromatic amines, and $(C_1-C_4)$-alkylpyridines.

5. The process according to claim 4, wherein the base is selected from the group consisting of trimethylamine, triethylamine, tripropylamine, tributylamine, triisobutylamine, tripentylamine, trihexylamine, dibutylmethylamine, dimethylamine or diethylamine, unsubstituted aniline or a substituted aniline, pyridine, piperidine, pyrrole, indole, pyrazine, pyrimidine, morpholine, pyrazole, imidazole, sodium bicarbonate, sodium carbonate, potassium bicarbonate, potassium carbonate, ammonium bicarbonate, sodium hydrogen phosphate, sodium dihydrogen phosphate, trisodium phosphate, potassium hydrogen phosphate, potassium dihydrogen phosphate, and tripotassium phosphate.

6. The process according to claim 1 wherein the base is sodium bicarbonate.

7. The process according to claim 1, wherein the solvent is selected from the group consisting of water-miscible solvents, mixtures thereof, and mixtures of water-miscible and water-immiscible solvents.

8. The process according to claim 7, wherein the solvent is selected from the group consisting of $(C_1-C_4)$-alcohols, ketones, and mixtures thereof.

9. The process according to claim 8, wherein the solvent is selected from methanol, ethanol, propanol, isopropanol, butanol, acetone, methyl ethyl ketone, mixture thereof, and mixtures with one or more of the group consisting of ethyl acetate, toluene, and dichloromethane.

10. The process according to claim 1, wherein crystallization occurs at a temperature that is greater than about 40° C.

11. The process according to claim 10, wherein the crystallization occurs at a temperature between about 41° C. and about 80° C.

12. The process according to claim 11, wherein the crystallization occurs at between about 50° C. and about 70° C.

13. The process according to claim 1, wherein the base corresponds to from about 100 mol % to about 115 mol % of the quantitatively determined amount of N-(4-trifluoromethylphenyl)-2-cyano-3-hyd roxycrotonamide.

14. The process according to claim 13 wherein the amount of N-(4-trifluoromethylphenyl)-2-cyano-3-hydroxycrotonamide is quantitatively determined by HPLC.

15. The process according to claim 1, wherein the base corresponds to from about 108 mol % to about 112 mol % of the quantitatively determined amount of N-(4-trifluoromethylphenyl)-2-cyano-3-hydroxycrotonamide.

16. The process according to claim 15, wherein the amount of N-(4-trifluoromethylphenyl)-2-cyano-3-hydroxycrotonamide is quantitatively determined by HPLC.

17. The process according to claim 1 wherein the amount of added base corresponds to from about 90 mol % to about 110 mol % of the quantitatively determined amount of N-(4-trifluoromethylphenyl)-2-cyano-3-hydroxycrotonamide.

18. The process according to claim 17, wherein the amount of N-(4-trifluoromethylphenyl)-2-cyano-3-hydroxycrotonamide is quantitatively determined by alkalimetric titration.

19. The process according to claim 1 wherein the amount of added base corresponds to from about 95 mol % to about 105 mol % of the quantitatively determined amount of N-(4-trifluoromethylphenyl)-2-cyano-3-hydroxycrotonamide.

20. The process according to claim 19, wherein the amount of N-(4-trifluoromethylphenyl)-2-cyano-3-hydroxycrotonamide is quantitatively determined by alkalimetric titration.

21. The process according to claim 1, wherein the amount of added base corresponds to from about 98 mol % to 102 mol % of the quantitatively determined amount of N-(4-trifluoromethylphenyl)-2-cyano-3-hydroxycrotonamide.

22. The process according to claim 21, wherein the amount of N-(4-trifluoromethylphenyl)-2-cyano-3-hydroxycrotonamide is quantitatively determined by alkalimetric titration.

23. The process according to claim 1, wherein crystals of a compound of formula I are added to the solution.

24. The process according to claim 1, wherein the solution obtained is filtered after adding base corresponding to from about 50 mol % to about 150 mol % of the amount of the quantitatively determined N-(4-trifluoromethylphenyl)-2-cyano-3-hydroxycrotonamide.

25. The process according to claim 1, as claimed in one or more of claims 1 to 8, wherein the mixture of organic solvent in water in step b) is heated to a temperature of from about 40° C. to about 85° C.

26. The process according to claim 1, wherein the ratio of organic solvent to water in step a) is from about 1:1 to about 8:1.

27. The process according to claim 26, wherein the ratio of organic solvent to water is from about 2:1 to about 6:1.

28. The process according to claim 27, wherein the ratio of organic solvent to water is from about 3:1 to about 5:1.

29. The process according to claim 1, wherein the ratio of organic solvent to water in step c) is from about 2:1 to about 0.6:1.

30. The process according to claim 29, wherein the ratio of organic solvent to water in step c) is from about 1.6:1 to about 0.8:1.

31. A process for separating a compound of formula I

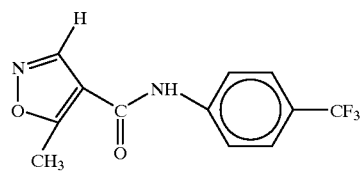

(I)

from a solution comprising an isopropanol-water mixture of between about 4:1 to 5:1 isopropanol to water, a compound of formula I, and N-(4-trifluoromethylphenyl)-2-cyano-3-hydroxycrotonamide; comprising:

a) quantitatively determining the amount of N-(4-trifluoromethylphenyl)-2-cyano-3-hydroxycrotonamide in the solution, b) adding sufficient $NaHCO_3$ to the solution which corresponds to between about 98 mol % and 102 mol % of the amount of the quantitatively determined amount of N-(4-trifluoromethylphenyl)-2-cyano-3-hydroxycrotonamide, c) changing the volume of the isopropanol-water mixture to a ratio of between about 2:1 to about 0.8:1 of isopropanol to water, and d) crystallizing the compound of formula I at between about 50° C. and about 70° C.

32. The process according to claim 31, further comprising the step of separating the crystals of the compound of formula I from the solution.

33. The process according to claim 31, further comprising the step of filtering the solution after step b).

* * * * *

UNITED STATES PATENT AND TRADEMARK OFFICE
CERTIFICATE OF CORRECTION

PATENT NO. : 6,303,792 B1
DATED : October 16, 2001
INVENTOR(S) : Hans-Hermann Lau et al.

It is certified that error appears in the above-identified patent and that said Letters Patent is hereby corrected as shown below:

<u>Column 9,</u>
Line 62, "n-(4" should read -- N-(4- --.

<u>Column 10,</u>
Line 42, "mixture" should read -- mixtures --.
Line 57, "hyd roxycrotonamide" should read -- hydroxycrotonamide --.

Signed and Sealed this

Third Day of September, 2002

Attest:

Attesting Officer

JAMES E. ROGAN
Director of the United States Patent and Trademark Office